(12) United States Patent
Bornzin et al.

(10) Patent No.: US 7,797,059 B1
(45) Date of Patent: Sep. 14, 2010

(54) SYSTEM AND METHOD FOR LEAD IMPLANTATION IN A PERICARDIAL SPACE

(75) Inventors: Gene A. Bornzin, Simi Valley, CA (US); Yougandh Chitre, Valencia, CA (US); John W. Poore, South Pasadena, CA (US)

(73) Assignee: Pacesetter, Inc., Sylmar, CA (US)

( * ) Notice: Subject to any disclaimer, the term of this patent is extended or adjusted under 35 U.S.C. 154(b) by 697 days.

(21) Appl. No.: 11/560,297

(22) Filed: Nov. 15, 2006

(51) Int. Cl.
*A61N 1/05* (2006.01)

(52) U.S. Cl. ...................................... 607/129; 607/116

(58) Field of Classification Search ................. 607/119, 607/122, 129, 116, 117; 128/785, 418; 239/107; 606/129
See application file for complete search history.

(56) References Cited

U.S. PATENT DOCUMENTS

| | | | | |
|---|---|---|---|---|
| 4,146,037 A * | 3/1979 | Flynn et al. | ................... | 607/131 |
| 4,207,903 A * | 6/1980 | O'Neill | ....................... | 607/131 |
| 4,938,231 A * | 7/1990 | Milijasevic et al. | ......... | 607/129 |
| 5,336,252 A * | 8/1994 | Cohen | ......................... | 607/119 |
| 5,464,447 A | 11/1995 | Fogarty et al. | | |
| 5,618,287 A | 4/1997 | Fogarty et al. | | |
| 5,665,107 A * | 9/1997 | Hammerslag | ................ | 606/214 |
| 5,690,648 A | 11/1997 | Fogarty et al. | | |
| 6,718,212 B2 * | 4/2004 | Parry et al. | ................... | 607/130 |
| 6,889,091 B2 * | 5/2005 | Hine et al. | .................... | 607/119 |
| 2003/0074041 A1 | 4/2003 | Parry et al. | | |
| 2004/0135008 A1 * | 7/2004 | Brax | ........................... | 239/493 |
| 2005/0177220 A1 | 8/2005 | Iaizzo et al. | | |

* cited by examiner

*Primary Examiner*—Carl H Layno
*Assistant Examiner*—Pamela M Bays

(57) ABSTRACT

A system for pericardial lead implantation is disclosed herein. The system includes an implantation tool and a stimulation lead. The implantation tool includes a tubular body, a first lumen, a second lumen, a stylet or guidewire, a first port, and a second port. The first and second lumens longitudinally extend through tubular body. The first port is in communication with the first lumen, and the second port is in communication with the second lumen. The stylet or guidewire is longitudinally displaceable in the first lumen and across the first port. A tissue adhesive is selectively administrable through the second port via the second lumen. The stimulation lead includes a distal end and an engagement feature. Placing the engagement feature in the first port and causing the stylet or guidewire to displace in a first direction across the first port causes the lead to attach to the implantation tool. Displacing the stylet or guidewire in a second direction opposite the first direction allows the lead to detach from the implantation tool.

19 Claims, 2 Drawing Sheets

SYSTEM AND METHOD FOR LEAD IMPLANTATION IN A PERICARDIAL SPACE

FIELD OF THE INVENTION

The present invention relates to medical devices and methods. More specifically, the present invention relates to devices and methods of implanting pacing and defibrillation leads.

BACKGROUND OF THE INVENTION

Factors (e.g., coronary sinus obstructions, absence of a suitable cardiac vein, high thresholds, or pheric nerve stimulation) warrant the need for an alternative to a transvenous approach to the implantation of left ventricle ("LV") leads in congestive heart failure ("CHF") patients in need of cardiac rhythm treatment ("CRT"). Historically, the alternative to a transvenous approach has entailed placement of an epicardial lead, which required invasive surgery and an associated hospital stay.

A minimally invasive pericardial approach to implanting a stimulating lead (e.g., a LV lead) has shown great promise as an alternative to the aforementioned transvenous and invasive surgery methods. In the pericardial approach, an introducer sheath is used to deliver a lead via a subxiphoid access to an implant location within the pericardial space. Visualization techniques, such as traditional fluoroscopy, MRI or endoscopy, are used to guide the introducer sheath to the implantation location within the pericardial space and to guide the final positioning of the lead. The pericardial approach is advantageous for a number of reasons. First, it does not require access to the vascular system. Second, it is minimally invasive and does not require surgical intervention and the associated general anesthesia. Third, it allows for a pathway to the entire exterior of the heart (e.g., any chamber, blood vessel or other anatomical feature of the heart) via a single entry point in the patient and in the pericardial sac. As a result, the minimally invasive pericardial approach offers greater simplicity and safety as compared to the transvenous and surgical approaches to stimulation lead implantation.

Despite the great promise shown by the minimally invasive pericardial approach, a current challenge continues to be an inability to reliably achieve a mechanically and electrically stable fixation of a stimulation lead at a preferred implantation site within the pericardial space. Consequently, there is a need in the art for a device and method that addresses the fixation challenge.

BRIEF SUMMARY

A system for pericardial lead implantation is disclosed herein. In one embodiment the system includes an implantation tool and a stimulation lead. The implantation tool includes a tubular body, a first lumen, a second lumen, a stylet or guidewire, a first port, and a second port. The first and second lumens longitudinally extend through tubular body. The first port is in communication with the first lumen, and the second port is in communication with the second lumen. The stylet or guidewire is longitudinally displaceable in the first lumen and across the first port. A tissue adhesive is selectively administrable through the second port via the second lumen. The stimulation lead includes a distal end and an engagement feature. Placing the engagement feature in the first port and causing the stylet or guidewire to displace in a first direction across the first port causes the lead to attach to the implantation tool. Displacing the stylet or guidewire in a second direction opposite the first direction allows the lead to detach from the implantation tool.

A method of pericardial lead implantation is disclosed herein. In one embodiment, the method includes placing an engagement feature of a stimulation lead in a first port of an implantation tool, extending a stylet or guidewire into the first port to attach the engagement feature to the implantation tool, and placing the attached implantation tool and stimulation lead in a pericardial space via a sub-xiphoid access.

A method of pericardial lead implantation is disclosed herein. In one embodiment, the method includes attaching a stimulation lead to an implantation tool, inserting the attached lead and tool into a pericardial space via a sub-xiphoid access, and applying a tissue adhesive from the tool to the lead.

While multiple embodiments are disclosed, still other embodiments of the present invention will become apparent to those skilled in the art from the following detailed description, which shows and describes illustrative embodiments of the invention. As will be realized, the invention is capable of modifications in various aspects, all without departing from the spirit and scope of the present invention. Accordingly, the drawings and detailed description are to be regarded as illustrative in nature and not restrictive.

DETAILED DESCRIPTION

An implant tool 10 and method for implanting a stimulation lead 15 (e.g., pacing and/or defibrillation lead) are disclosed herein. The implant tool 10 and method are advantageous in that they allow a lead 15 to be slid into position within the pericardial space 20 and then dropped to achieve a mechanically and electrically stable atraumatic fixation to the implant location.

Figure 1:
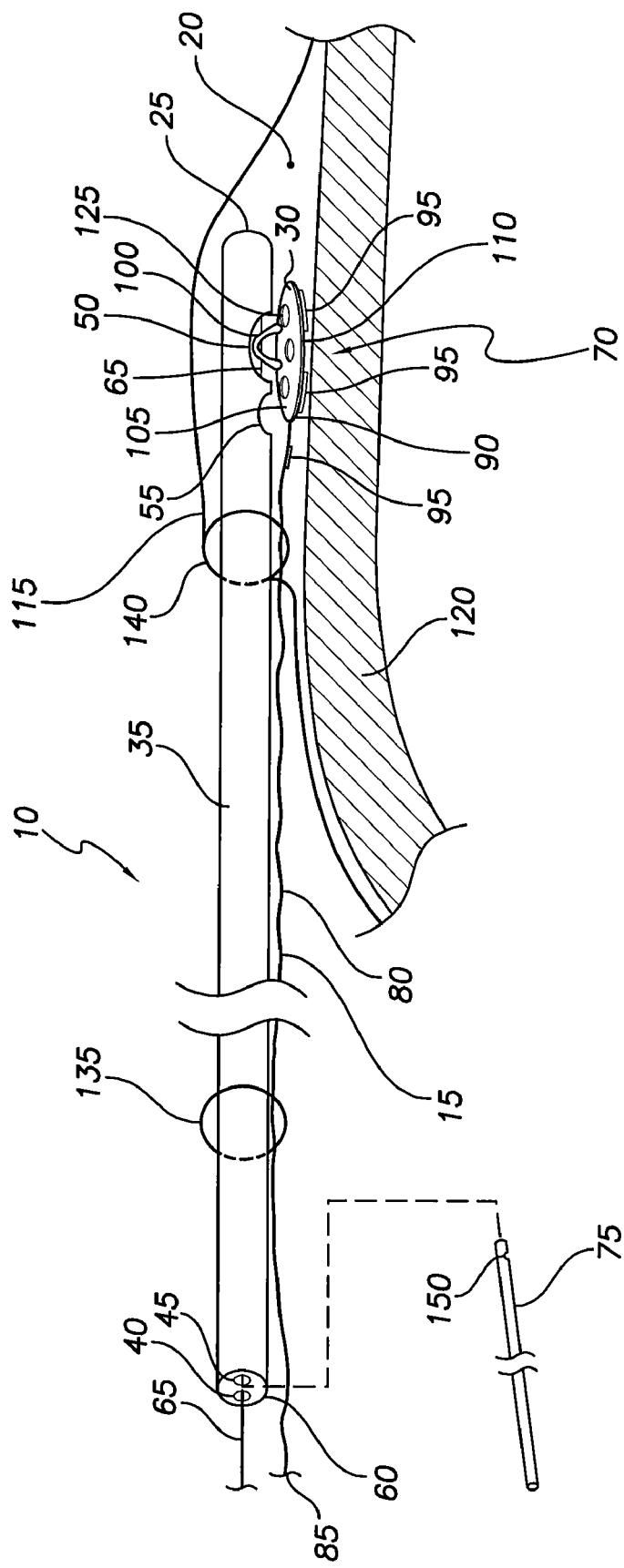
FIG. 1 is a diagrammatic depiction of a distal end of the implant tool located within the pericardial space and coupled to a distal end of the lead.

For a discussion of the device 10, reference is made to FIG. 1, which is a diagrammatic depiction of a distal end 25 of the implant tool 10 located within the pericardial space 20 and coupled to a distal end 30 of the lead 15. As shown in FIG. 1, the tool 10 includes a tubular body 35, a first lumen 40, a second lumen 45, a first port 50 and a second port 55. The tubular body 35 includes distal and proximal ends 25, 60. The first lumen 40 extends the length of the tubular body 35 and daylights or opens at the distal and proximal ends 25, 60. The first port 50 connects to the first lumen 40 and opens through the wall of the tubular body 35 near the distal end 25. The second lumen 45 daylights or opens at the proximal end 60 and extends nearly the length of the tubular body 35 to connect to the second port 55, which opens through the wall of the tubular body 35 near the distal end 25.

As depicted in FIG. 1, the first lumen 40 slideably displaceably receives a stylet or guidewire 65, which is used to direct the tool 10 to the implant site 70 within the pericardial space 20. When the stylet or guidewire 65 is fully distally extended through the first lumen 40, the stylet or guidewire 65 extends through the first port 50 and, as discussed later in this Detailed Description, is used to releasably couple the lead distal end 30 to the tool body 35.

In one embodiment, the stylet or guidewire 65 is composed of a shape memory alloy (e.g., Nitinol®, etc.), a super polymer (e.g., polyether block amides ("PEBAX"), polyetheretherketone ("PEEK"), high density polyethylene ("HDPE") etc.), or a metal or alloy (e.g., stainless steel, MP35N, Ti, or etc.). Regardless of the material from which the stylet or guidewire 65 is built, the stylet or guidewire 65 is deflectable to assist in its negotiating a path to the implantation site 70.

As can be understood from FIG. 1, in one embodiment, the second lumen 45 slideably displaceably receives an extendable/retractable sheath 75, which, as discussed later in this Detailed Description, is used to dispense a tissue adhesive through the second port 55. In another embodiment, the tissue adhesive is administered through the second lumen 45 without the use of the sheath 75.

As illustrated in FIG. 1, the pacing and/or defibrillation lead 15 includes a longitudinally extending body 80, a proximal end 85 and a distal end 30. In one embodiment, the lead body 80 is composed of silicone, polyurethane or a combination thereof.

The lead distal end 30 includes a member 90, electrodes 95 mounted on the member 90, and a connection feature 100 extending from the member 90. In one embodiment, the member 90 is a planar disc 90 that has a circular, elliptical, rectangular, or etc. shape. The disc 90 has a superior side 105 and an inferior side 110. When the lead 15 is implanted in the pericardial space 20, the superior side 105 abuts against the interior surface of the pericardial sac 115, and the inferior side 110 abuts against the exterior or myocardial surface of the heart wall 120. In one embodiment, the disc 90 is a non-resorbable polymer mesh, weave, fabric, etc. (e.g., Dacron® mesh). In one embodiment, the disc 90 includes holes 125 that extend through the disc 90 to form receptacles for receiving the adhesive and bonding the disc 90 to the pericardial sac 115 and the heart wall 120.

As indicated in FIG. 1, the connection feature 100 extends from the superior side 105 of the disc 90, and the electrodes 95 extend from the inferior side 110 of the disc 90. In one embodiment, the connection feature 100 is a hook or loop 100, which, as discussed later in this Detailed Description, receives the stylet or guidewire 65 when the stylet or guidewire 65 is fully distally displaced within the first lumen 40. In one embodiment, the connection feature 100 is formed of a metal or alloy (e.g., stainless steel, MP35N, Ti, or etc.). In one embodiment, the connection feature 100 is formed of a polymer (e.g., PEBAX, PEEK, HDPE, or etc.).

In one embodiment, the electrodes 95 are independently circuited. In one embodiment, the electrodes 95 are ganged together off of common circuit. In one embodiment, the electrodes 95 are in wireless communication with the implanted pacing and/or defibrillation device.

In one embodiment, the electrodes are formed of an electrically conductive metal or alloy (e.g., platinum-iridium alloy, titanium, or etc.). In one embodiment, the electrodes are formed of an electrically conductive polymer (e.g., silicone rubber impregnated with gold or platinum particles, or etc.). In one embodiment, at least one shock electrode 95 is located along the length of the lead body. In one embodiment, at least one shock electrode 95 is located on the disc 30 with the rest of the electrodes 95, which, in one embodiment, are pacing and/or sensing electrodes 95.

In one embodiment, a suitable amount of steroid (e.g., dexamethasone sodium phosphate, etc.) is accommodated proximal to the electrodes for low capture threshold levels.

Figure 2:
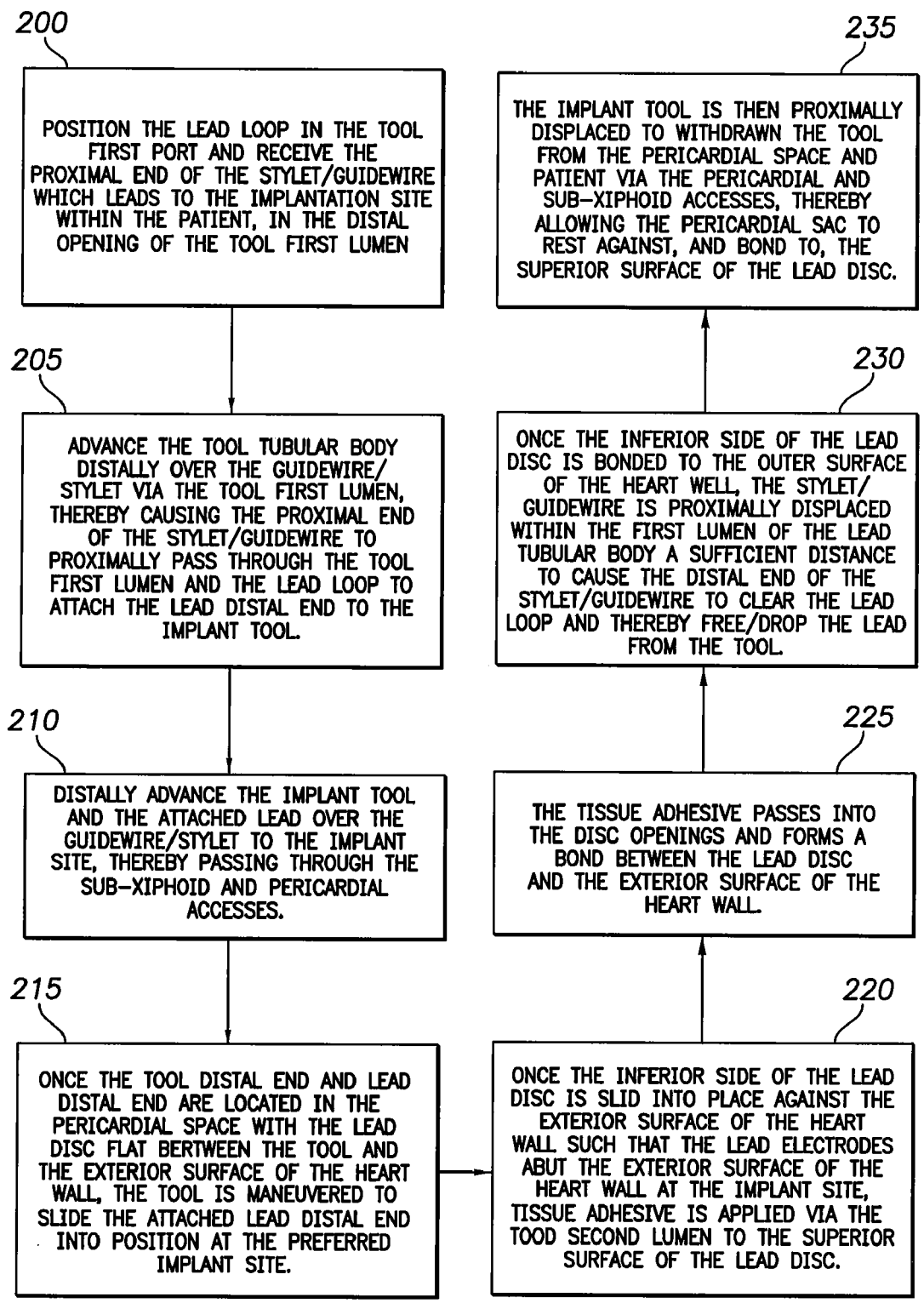
FIG. 2 is a flow chart outlining the method of implanting the lead via the tool.

For a discussion of a method of utilizing the tool 10 to implant the lead 15, reference is made to FIGS. 1 and 2. FIG. 2 is a flow chart outlining the method of implanting the lead 15 via the tool 10. As can be understood from FIGS. 1 and 2, in one embodiment, an introducer sheath and the stylet/guidewire 65 extending there through are routed through a sub-xiphiod access 135 in a patient and into the pericardial space 20 via a pericardial access 140. The stylet/guidewire 65, a Touhy needle or other device known in the art and routed to the pericardial sac 115 via the introducer sheath is used to form the pericardial access 140.

In one embodiment, the distal end of the introducer sheath and guidewire/stylet 65 are then positioned at the implant site 70 within the pericardial space 20 to guide the implant tool 10 and attached lead 15 to the implant site 70. In another embodiment, the introducer lead is withdrawn and the guidewire/stylet 65 alone is used to guide the implant tool 10 and attached lead to the implant site 70.

The lead loop 100 is positioned in the tool first port 50, and the distal opening of the tool first lumen 40 receives the proximal end of the guidewire/stylet 65, which still extends distally into implant site 70 within the patient [block 200]. As the tool tubular body 35 advances distally over the guidewire/stylet 65 via the tool first lumen 40, the proximal end of the stylet/guidewire 65 proximally passes through the tool first lumen 40 and the lead loop 100 to attach the lead distal end 30 to the implant tool 10 [block 205].

As the implant tool 10 and the attached lead 15 are distally advanced over the guidewire/stylet 65 to the implant site 70, the tool 10 and attached lead 15 pass through the sub-xiphoid access 135 and the pericardial access 140 [block 210]. As previously mentioned, in one embodiment, as the tool 10 and attached lead 15 travel over the guidewire/stylet 65 to the implant site 70, the tool 10 and attached lead 15 pass through the introducer sheath. In another embodiment, the tool 10 and attached lead 15 travel over the guidewire/stylet 65 to the implant site 70 without use of an introducer sheath.

Once the tool 10 and attached lead 15 are positioned as depicted in FIG. 1 such that the tool distal end 25 and lead distal end 30 are located in the pericardial space 20 with the lead disc 90 flat between the tool 10 and the exterior surface of the heart wall 120, the tool 10 is maneuvered to slide the attached lead distal end 30 into position at the preferred implant site 70 [block 215]. Once the inferior side 110 of the lead disc 90 is slid into place against the exterior surface of the heart wall 120 such that the lead electrodes 95 abut the exterior surface of the heart wall 120 at the implant site 70, tissue adhesive is applied via the tool second lumen 45 to the superior surface 105 of the lead disc 110 [block 220]. The tissue adhesive passes into the disc openings 125 and forms a bond between the lead disc 105 and the exterior surface of the heart wall 120 [block 225].

In one embodiment, the tissue adhesive is applied via the extendable/retractable sheath 75 located in the tool second lumen 45. When the sheath 75 is proximally displaced within the tool second lumen 45, the distal end of the sheath 75 opens into the second tool port 55, which allows tissue adhesive to exit the sheath 75 onto the lead disc 90. When the sheath 75 is returned to its fully distal position, tissue adhesive is prevented from exiting the second tool port 55.

In one embodiment, the tissue adhesive is applied via the extendable/retractable sheath 75 located in the tool second lumen 45. When the sheath 75 is proximally displaced within the tool second lumen 45, a port 150 in the sidewall of the sheath 75 aligns with and opens into the second tool port 55, which allows tissue adhesive to exit the sheath 75 onto the lead disc 90. When the sheath 75 is returned to its fully distal position, the sheath port 150 and the second port 55 no longer align, and tissue adhesive is prevented from exiting the second tool port 55.

In one embodiment, the tissue adhesive is applied via a sheath 75 that is rotatable within the tool second lumen 45 and includes a port 150 in the sidewall of the sheath 75. When the sheath 75 is rotated such that its port 150 aligns with and opens into the second port 55, tissue adhesive can exit the sheath 75 onto the lead disc 90. When the sheath 75 is rotate back such that the sheath port 150 no longer aligns with the second port 55, tissue adhesive is prevented from exiting the second tool port 55.

In one embodiment, the tissue adhesive is applied via the tool second lumen 45 without the use of the extendable/retractable sheath 75. In such an embodiment, the tissue adhesive is simply injected through the tool second lumen 45 when it is desired to apply the tissue adhesive to the lead disc 90. When the application of tissue adhesive is no longer desired, the tissue adhesive injection is terminated.

In one embodiment, the adhesive is cyanoacrylate. In one embodiment, the adhesive is an extracellular matrix ("ECM") (e.g., fibronectin, collagen, vitronectin, combinations thereof, etc.).

In one embodiment, the tool tubular body 35 further includes a third lumen. In such an embodiment, a fibrin glue (e.g., Tisseel®, Baxter®, etc.) is applied via the second lumen 45 (e.g., as already mentioned, by using the extendable/retractable sheath 75 in the second lumen 45 or simply using the second lumen 45 by itself), and an activator is applied via the third lumen in manner similar that used with the second lumen 45.

Once the inferior side 110 of the lead disc 90 is bonded to the outer surface of the heart wall 120, the stylet/guidewire 65 is proximally displaced within the first lumen 40 of the lead tubular body 35 a sufficient distance to cause the distal end of the stylet/guidewire 65 to clear the lead loop 100 and thereby free/drop the lead 15 from the tool 10 [block 230]. The implant tool 10 is then proximally displaced to withdraw the tool 10 from the pericardial space 20 and patient via the pericardial and sub-xiphoid accesses 140, 135 [block 235]. Once the tool distal end 25 vacates the pericardial space 20, the elasticity of the pericardial sac 115 brings the inner surface of the pericardial sac 115 into abutting contact with the superior surface 105 of the lead disc 90. The tissue adhesive bonds the inner surface of the pericardial sac 115 to the superior surface 105 of the lead disc 90. As a result, lead disc 90 is sandwiched between, and bonded to, the pericardial sac 115 and the exterior surface of the heart wall 120.

In one embodiment, the adhesive bonds provide an electrically and mechanically stable atraumatic fixation of the lead electrodes 95 to the implant site 70 that is sufficiently permanent for the operational life associated with the lead 15. In one embodiment, the lead disc 90 is made of a non-resorbable mesh or weave material (e.g., Dacron®). As a result, tissue in-growth from the pericardial sac 115 and/or the outer surface of the heart wall 120 soon permanently attaches the lead disc 90 to the implantation site 70 to create an electrically and mechanically stable atraumatic fixation of the lead electrodes 95 to the implantation site 70.

As can be understood from the preceding discussion, the lead implantation system disclosed herein is advantageous because it allows a lead 15 to be slid into place and dropped at the implantation site 70, thereby facilitating quick and accurate placement of the lead electrodes 95. The lead implantation system and method disclosed herein provides an easy and time efficient way of creating an electrically and mechanically stable atraumatic fixation of the lead electrodes 95 to the implantation site 70.

Although the present invention has been described with reference to preferred embodiments, persons skilled in the art will recognize that changes may be made in form and detail without departing from the spirit and scope of the invention.

What is claimed is:

1. A system for pericardial lead implantation, the system comprising:
    an implantation tool including a tubular body including a first longitudinally extending lumen, a stylet or guidewire longitudinally displaceable in the first lumen, and a first port in communication with the first lumen and across which the stylet or guidewire is displaceable; and
    a pericardial stimulation lead comprising an engagement feature that is adapted for placement in the first port and configured to be held in the first port by engagement by the stylet or guidewire.

2. The system of claim 1, wherein a distal end of the stylet or guidewire is displaceable across the first port.

3. The system of claim 1, wherein the first port is near a distal end of the tubular body.

4. The system of claim 1, wherein the implantation tool further includes a second lumen and a second port in communication with the second lumen.

5. The system of claim 4, wherein the implantation tool further includes a tissue adhesive passing through the second lumen to the second port.

6. The system of claim 5, wherein the implantation tool further includes a sheath displaceable in the second lumen to control the passing of the adhesive through the second port.

7. The system of claim 6, wherein displacement of the sheath to a first position allows the adhesive to pass through the second port, and displacement of the sheath to a second position prevents the adhesive from passing through the second port.

8. The system of claim 1, wherein the engagement feature is a hook or a loop.

9. The system of claim 1, wherein the distal end of the lead includes a disc from which the engagement feature extends.

10. The system of claim 9, wherein the disc includes at least one hole extending there through.

11. The system of claim 9, wherein the disc is formed from a non-resorbable mesh or weave material.

12. The system of claim 11, wherein the material is polyethylene terephthalate.

13. The system of claim 9, wherein the disc includes an electrode on a side of the disc opposite a side from which the engagement feature extends.

14. The system of claim 1, wherein the engagement feature is configured to be releasably engaged by the stylet or guidewire.

15. The system of claim 1, wherein the engagement feature of the stimulation lead is configured to be released from the first port by retraction of the stylet or guidewire.

16. A system for pericardial lead implantation, the system comprising:
    an implantation tool and a pericardial stimulation lead adapted for extension along the exterior of the implantation tool, the implantation tool including a first means for engaging the stimulation lead, the stimulation lead including second means adapted for placement in the first means and engagement with the first means while the stimulation lead is extended along the exterior of the implantation tool; and
    a stylet or guidewire configured to cooperate with the first and second means for engaging such that in an extended position within the implantation tool the stylet or guidewire causes the first and second means to engage the implantation tool and the stimulation lead, and in a retracted position the stylet or guidewire causes the first and second means to disengage.

17. A method of pericardial lead implantation, the method comprising:
  placing an engagement feature of a pericardial stimulation lead in a first port of an implantation tool;
  extending a stylet or guidewire into the first port to attach the engagement feature to the implantation tool;
  placing the attached implantation tool and stimulation lead in a pericardial space via a sub-xiphoid access; and
  at least partially withdrawing the stylet or guidewire from the first port to detach the engagement feature from the implantation tool.

18. The method of claim 17, further comprising discharging a tissue adhesive from a second port of the implantation tool.

19. The method of claim 17, further comprising adhering the lead to a pericardial sac and/or a heart surface via tissue in-growth.

* * * * *